Figure 1:
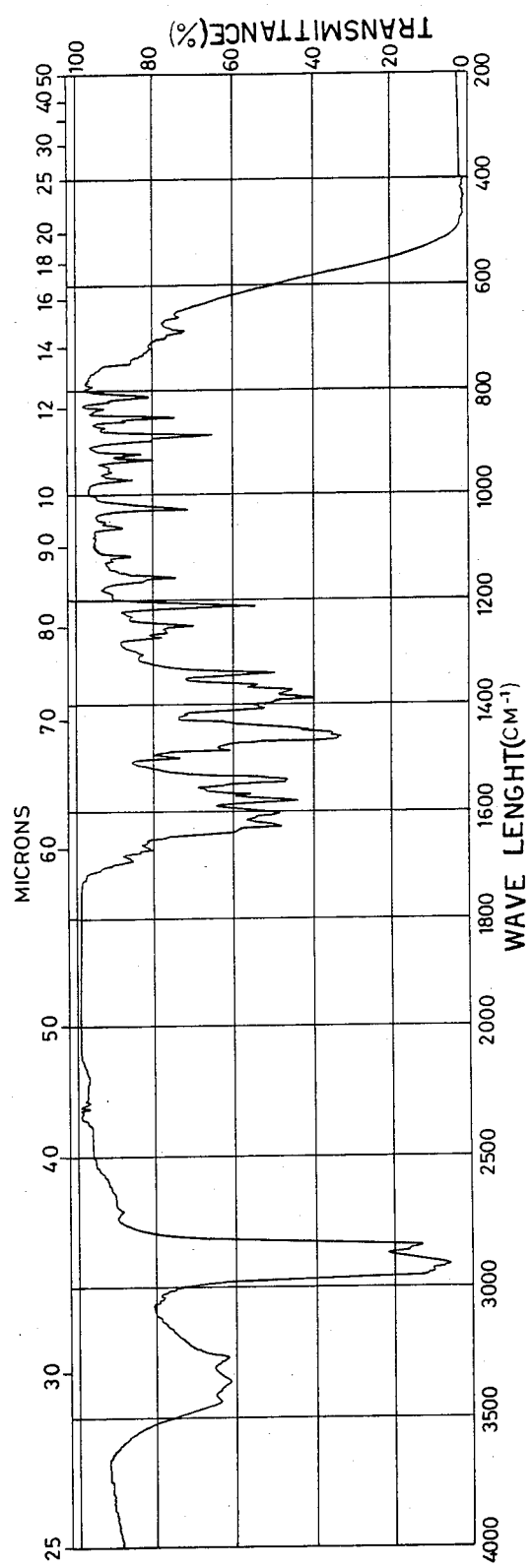

United States Patent [19]

Colombi

[11] Patent Number: 4,672,077

[45] Date of Patent: Jun. 9, 1987

[54] NOVEL SOLUBLE SALT HAVING ANALGESIC AND ANTI-INFLAMMATORY ACTIVITY, A PROCESS FOR THE PREPARATION THEREOF AND PHARMACEUTICAL FORMS CONTAINING THEM

[75] Inventor: Nelly Colombi, Castano, Italy

[73] Assignee: Istituto Biochimico Pavese SPA, Pavia, Italy

[21] Appl. No.: 869,911

[22] Filed: Jun. 3, 1986

[51] Int. Cl.$^4$ .................. C07C 101/12; A61K 31/085; A61K 31/135; A61K 31/14

[52] U.S. Cl. ................................ 514/555; 260/501.13

[58] Field of Search ................... 260/501.13; 514/555

[56] References Cited

U.S. PATENT DOCUMENTS

| 2,794,045 | 5/1957 | Beaufour et al. | 260/501.13 |
| 3,002,886 | 10/1961 | Halpern | 260/501.13 |
| 3,242,048 | 3/1966 | Straub et al. | 260/501.13 |
| 4,080,472 | 3/1978 | Bohuon | 514/555 |
| 4,279,926 | 7/1981 | Bruzzese et al. | 514/555 |

FOREIGN PATENT DOCUMENTS

| 1195767 | 7/1965 | Fed. Rep. of Germany | 260/501.13 |
| 1391M | 7/1962 | France | 260/501.13 |
| 1126605 | 9/1968 | United Kingdom | 260/501.13 |

*Primary Examiner*—J. E. Evans
*Attorney, Agent, or Firm*—Murray and Whisenhunt

[57] ABSTRACT

The D-6-methoxy-alpha-methyl-2-naphthalenacetate of 1-carboxy-N-N',N''-trimethylmethanamine sodium salt, which is prepared by reacting 1-carboxy-N,N',N''-trimethylmethanamine sodium salt and D-6 methoxymethyl-2-naphtalenacetic acid, at a temperature of between 10° and 30° C., shows a better and more ready absorption and higher tolerability at the level of the gastric mucosa.

3 Claims, 2 Drawing Figures

NOVEL SOLUBLE SALT HAVING ANALGESIC AND ANTI-INFLAMMATORY ACTIVITY, A PROCESS FOR THE PREPARATION THEREOF AND PHARMACEUTICAL FORMS CONTAINING THEM

The present invention relates to the preparation and use in pharmaceutical field of a novel saline derivative of the D-6 methoxy-alpha-methyl-2-naphthalenacetic acid.

The subject compound can be chemically defined as the D-6-methoxy-alpha-methyl-2-naphtalenacetate of 1-carboxy, N,N',N''-trimethylmethanamine sodium salt showing the following structural formula:

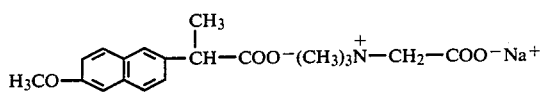

The anti-inflammatory and analgesic activity of D-6 methoxy-alpha-methyl-naphtalenacetic acid and the use thereof in pharmaceutical forms for oral and rectal use are known, said activity being accompanied by a relevant ulcerogenic activity both at the level of the gastric mucosa, and at the level of the intestinal mucosa, with troubles such as the possibly limitation of the use especially when a long term therapy is to be carried out.

The subject salt, showing instantaneous solubility in water, and a pH in solution of 7.2–7.5, permits two main results to be achieved in its practical use:

(1) A much more ready and much more immediate pharmakinetics with respect to the D-6 methoxy-alpha-methyl-2-napthalenacetic acid, which permits the use of lower amounts of the drug with the same effects.

(2) A tolerability at the level of the gastric mucosa higher than that of the D-6 methoxy-alpha-methyl-2-naphtalenacetic acid, since the salt is neutral and extremely soluble avoiding the untolerance arising from its contact upon the tablet is dissolved or the capsule is dispersed.

Owing to its immediate solubility in water the novel salt permits the preparation of all the pharmaceutical forms by oral, rectal, injective, topical route to be carried out, such as tablets, capsules small envelopes, syrups, suppositories, ovules, lavages, simple or liophylized ampoules gels or ointments, as well as of all the pharmaceutical forms with controlled and/or delayed release of the drug. To this end the active principle is combined with the standard excipients, vehicles, solvents, fillers etc. well known in the pharmaceutical field, and the preparation of the pharmaceutical forms takes place according to the usual and well known galenical techniques and technologies.

The D-6 methoxy-alpha-methyl-2-naphtalenacetate of 1-carboxy-N,N',-N''-trimethylmethanamine sodium salt is chemically prepared through a process characterized by reacting 1-carboxy-N,-N',N''-trimethylmethanamine sodium salt dissolved in water, in a water soluble organic solvent such as for instance acetone in which D-6-methoxy-methyl-2-naphtalenacetic acid has been previously solubilized.

The salification takes place at a temperature of between 10° C. and 30° C., better at room temperature. The thus obtained salt is soluble in the salification medium and it can be obtained in crystalline form by pouring it into an excess of the organic solvent used for the solubilization of D-6 methoxy-alpha-methyl-2-naphtalenacetic acid.

EXAMPLE 5 g of D-6 methoxy-alpha-methyl-2-naphthalenacetic acid (0.0217 moles) are dissolved in 15 ml of acetone.

Separately 2.9 g (0.0217 moles) of 1-carboxy-N,N',N''-trimethylmethanamine monohydrate are dissolved in 3 ml of water, which is converted into sodium form by pouring 0.87 g (0.0217 moles) of NaOH dissolved in 1 ml of water.

The obtained solution is poured in the acetonic solution of D-6 methoxy-alpha-methyl-2-naphthalenacetic acid.

A clear, light yellow phase is obtained that is concentrated up ¼ of volume, and is added as a thin stream into 100 ml of acetone obtaining a white crystalline precipitate that upon being filtered, washed with acetone and oven dried under vacuum, weights 6.8 g. Yield 93.6%.

The product has a m.p. 154°–156° C. and pH in a 10% water solution from 7.1 to 7.4.

Figure 2:
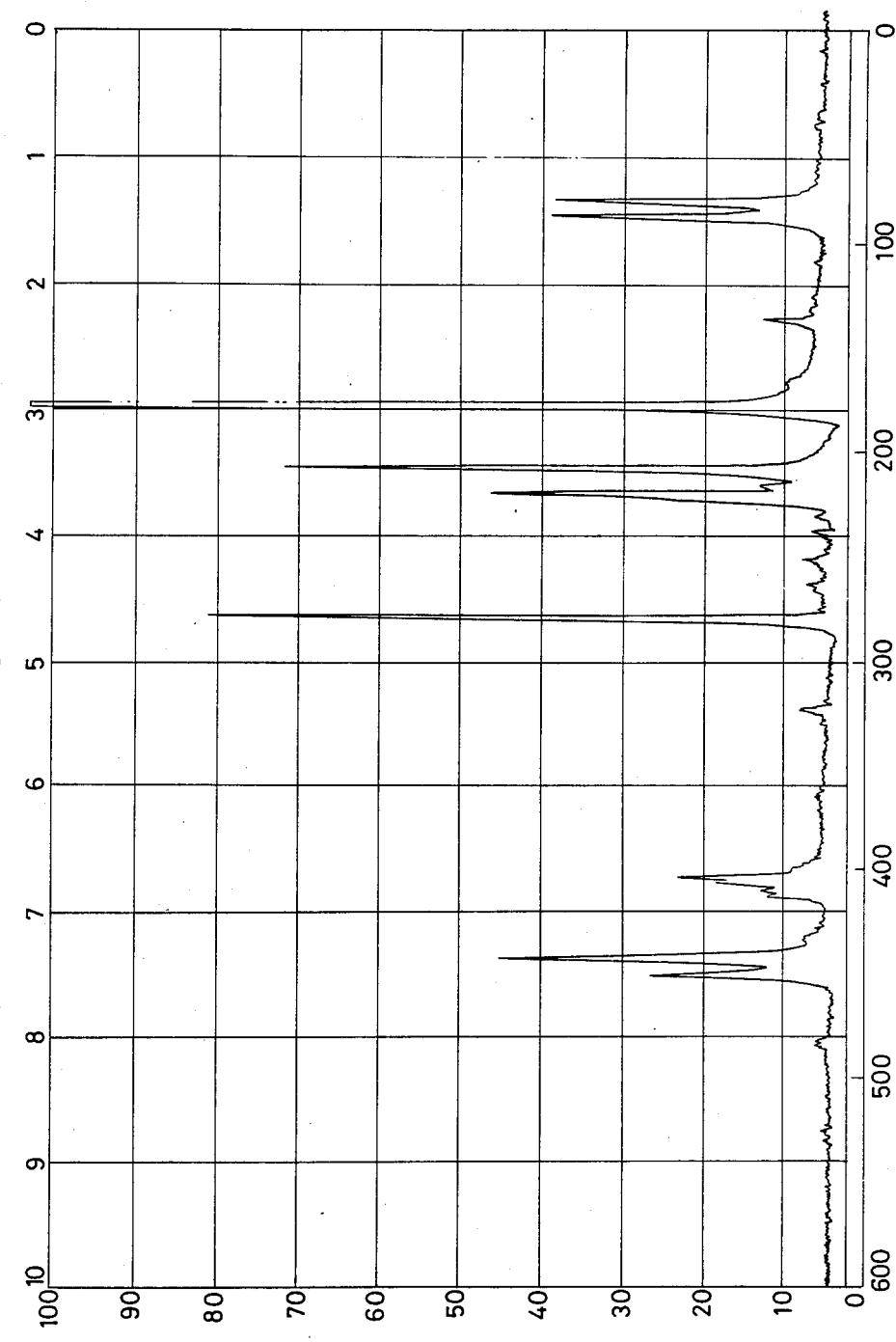

The characterizing spectrum has been carried out in comparison with the starting products with the crystallographic system, finding that a new crystalline form is formed defined as shown in the enclosed spectra in which the FIG. 1 shows the infrared spectrum and the FIG. 2 the magnetic nuclear resonance spectrum.

From the pharmacotoxicological view point the derivative according to the invention presents the following important data:

(A) TOXICITY

The acute toxicity has been tested in the rat and in the mouse with the following results:
LD 50 in the mouse per os: 1502 mg/kg;
LD 50 in the mouse per i.p.: 1214 mg/kg;
LD 50 in the rat per os: 925 mg/kg;
LD 50 in the rat per i.p.: 736 mg/kg.

(B) ULCEROGENIC ACTIVITY

It has been evaluated in the rat per os, after 7 days, in comparison with the NAPROXEN, with the following values of UD 50:
Naproxen: 97.5 mg/kg;
Compound of the invention: 271.3 mg/kg.

(C) ANTI-INFLAMMATORY ACTIVITY

It has been evaluated in the rat with the carrageneen induced oedema test:
ED 50=21,43 mg/kg.

(D) ANALGESIC ACTIVITY

It has been evaluated in the mouse with the Writhing test, finding ED 50=29,73 mg/kg.

(E) ANTIPIRETIC ACTIVITY

In the standard test it has been found ED 50=23,28 mg/kg.

I claim:

1. D-6-methoxy-alfa-methyl-2-naphthalenacetate of 1-carboxy-N-N'-N''-trimethylmethanamine sodium salt having general formula:

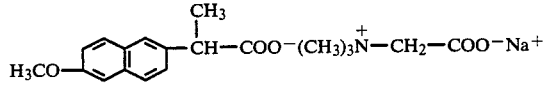

2. Pharmaceutical composition, characterized by containing as the active ingredient the derivative according to claim 1, together with the common excipients and vehicles pharmaceutically acceptable.

3. Pharmaceutical composition according to claim 2, characterized by being in form suitable for the oral, rectal, injectable or topical administration.

* * * * *